United States Patent [19]
Kushner

[11] Patent Number: 5,741,509
[45] Date of Patent: Apr. 21, 1998

[54] SILICONE WOUND DRESSING

[75] Inventor: Jack Kushner, Paso Robles, Calif.

[73] Assignee: Alvin S. Berlat, Silverdale, Wash.

[21] Appl. No.: 703,324

[22] Filed: Aug. 26, 1996

[51] Int. Cl.$^6$ .................................................. A61F 13/00
[52] U.S. Cl. .................... 424/443; 424/445; 514/944; 514/969
[58] Field of Search .................... 424/448, 449, 424/445, 443; 514/944, 969

[56] References Cited

U.S. PATENT DOCUMENTS

| | | | |
|---|---|---|---|
| 4,865,920 | 9/1989 | Sweet | 428/447 |
| 4,954,344 | 9/1990 | Gale | 424/448 |
| 5,162,410 | 11/1992 | Sweet | 524/266 |
| 5,292,530 | 3/1994 | McCrea | 424/66 |
| 5,413,792 | 5/1995 | Ninomiya | 424/434 |

*Primary Examiner*—D. Gabrielle Phelan
*Attorney, Agent, or Firm*—Norman Friedland; Marvin S. Aronoff

[57] ABSTRACT

A wound dressing is provided which comprises a blend of silicone fluid and fumed silica having the consistency of a stiff cream prepared in the presence of a volatile diluent that reduces the consistency of the silicon fluid-fumed silica blend to that of a spreadable cream or grease which can applied to a wound without producing further injury or undue discomfort. After the blend is in place on the wound, evaporation of the volatile diluent restores the consistency of the silicone fluid silica blend to its undiluted state, thereby allowing the advantages of increased wound adhesion and "smear proofing" to be achieved without producing further damage to the wound or undue pain and discomfort during application. The consistency of any particular blend of silicone fluid and fumed silica may be adjusted by varying the quantity of volatile diluent, thereby allowing the physician to vary the thickness of the film to help control the loss of water from the protected area.

14 Claims, No Drawings

5,741,509

SILICONE WOUND DRESSING

BACKGROUND OF THE INVENTION

This invention deals with the field of wound dressings and especially dressings designed for the treatment or prevention of scars resulting from injury or surgery.

Damage to the skin produced by injury or surgery often produces scars instead of the regeneration of the original tissue. While such scars on parts of the body that are ordinarily visible are undesirable as they may create obvious, embarrassing cosmetic problems, they are also very undesirable even on parts of the body which are normally covered. Such scar tissue lacks the functionality of normal skin. For example, the sense of touch may be diminished or completely lost and weak spots are created at locations where such scars join uninjured tissue.

Surgeons and doctors have historically sought and developed procedures, treatments, aftercare coverings, oils and a variety of wound dressings including synthetic skin to lessen the formation of scars. In addition, various procedures and treatments have been tried by the medical profession to ameliorate existing scars.

None of these previous treatments has proven to be totally successful and even the very best of these, such as water bearing plastic films or hydrogels have serious shortcomings. Since such hydrogel dressings do not conform well to the changing topography of the body they press harder at some points than at other points and may not completely cover all injured areas. As the water content of such hydrogel dressings will vary with atmospheric humidity, thus altering their effectiveness and lifetime, a covering or topcoat over the hydrogel sheet is often necessary. The complete hydrogel dressing is heavy, awkward and very difficult to maintain in proper position. Such dressings often require professional attention for proper maintenance. Once released from professional nursing care it is very doubtful that the patient alone or the patient's family can continue the process of maintaining the hydrogel dressing effectively.

A wound dressing designed for the treatment or prevention of scars resulting from injury or surgery should permit easy application to an injured or scarred area without causing undue pain or further damage to the injured tissue. Such a dressing should provide a permeable film over the injured area that would permit the natural transpiration of water vapor and other gases from the underlying tissue. In addition, the permeable film should be nearly weightless and should substantially completely cover any desired area with a thin, uniform, compliant film. Such a wound dressing film should also be generally waterproof or hydrophobic so that as a consequence of such hydrophobicity the film would resist the penetration of pathogenic organisms that require a water pathway to get past the film to the tissue beneath.

Furthermore, the wound dressing film should be made of materials that do not support the growth of pathogens. The wound dressing film must also remain intact when the underlying surface wrinkles, stretches or flexes and should not resist such changes in the underlying surface. The materials from which such a wound dressing is formed must be inert in contact with the wound surface and the surrounding tissue and must not exhibit any harmful effect when used correctly for its intended purpose. The wound dressing film should also have sufficient adhesion to the underlying surface that it protects so that a deliberate effort is required to remove it completely. Ideally, the material comprising such a film would be adjustable in consistency so that the thickness of the film can be varied as needed by the physician to help control loss of water from the protected area.

Many of the above requirements may be met with medical grade silicone oils, also known as siloxanes. Although such oils meet the biological properties required for this application and in addition have a very good record of compatibility with human tissue, they do not have the physical consistency which would make them suitable for use as wound dressings. Generally these materials are too fluid and oily for use as a wound dressing. Generally the consistency of a stiff cream or grease is desirable for the wound dressing when it is in place on the wound. Therefore, physical properties of silicone oils, such as viscosity, must be altered to achieve such a consistency. The desired consistency can be obtained by blending a relatively viscous silicone oil with fumed silica. Typically a silicone oil having a viscosity of at least about 5000 centistokes or higher can be blended with fumed silica to obtain the consistency of a stiff cream or grease. Such blends have been known for a long time and are well documented as a means of converting most oils to the consistency of a grease.

For example, a blend of a silicone fluid having a viscosity of 30,000 centistokes (manufactured by Dow-Corning Inc. and others) with fumed silica having from about 2% to about 3% by weight of fumed silica produces a suitable wound dressing. Although such a blend provides a vast improvement in consistency over the unblended silicone fluid, a much more viscous blend than this composition is desirable to improve adhesion to the wound and to prevent the dressing from smearing (i.e. "smear-proofing"). However, blends having the consistency to provide improved adhesion and "smear-proofing" are too difficult to apply to injured skin without causing further injury and pain. As a result, a compromise must be made in which a wound dressing having a more fluid consistency than would be ideal for a wound covering is used in order to avoid further injury and pain during application. This compromise in consistency has severely limited the use of such silicone based wound dressings in some situations.

There is a need for a silicone based wound dressing having high viscosity and thereby increased wound adhesion that can be used on wounds to prevent scarring without causing undue pain or further injury when it is applied. There is a further need for a silicone wound dressing that does not easily smear. Yet another need is for a method of applying high viscosity wound dressings to a wounded area without causing further injury or undue pain. A still further need is for a silicone wound dressing that can conveniently provide coatings of varying thickness to control water loss from the wound.

BRIEF DESCRIPTION OF THE INVENTION

The present invention is directed to meeting the foregoing needs by providing a wound dressing composition comprising silicone oils, fumed silica and a volatile diluent. Blends of non-volatile silicone fluid and fumed silica having the consistency of a stiff cream are prepared with a volatile diluent that reduces the consistency of the silicon fluid fumed silica blend to that of a spreadable cream or grease which can be applied to a wound without producing further injury or undue discomfort. After the blend is in place on the wound, evaporation of the volatile diluent restores the consistency of the silicone fluid silica blend to its undiluted state, thereby allowing the advantages of increased wound adhesion and "smear proofing" to be achieved without producing further damage to the wound or undue pain and discomfort during application. The consistency of any particular blend of silicone fluid and fumed silica may be adjusted by varying the quantity of volatile diluent, thereby allowing the physician to vary the thickness of the film to help control the loss of water frown tile protected area.

DESCRIPTION OF THE PREFERRED EMBODIMENTS

The wound dressing of the present invention comprises a blend of non-volatile silicone oil and fumed silica having the consistency of a stiff cream or grease, and a volatile diluent which in combination with the non-volatile silicone oil and fumed silica blend forms a composition having tile consistency of an oil or a light grease. The blend of silicone oil, fumed silica and volatile diluent is coated on an injured area of the body so that a film or coating is formed that covers the injured area. The volatile diluent rapidly evaporates from the film formed by the mixture of silicone oil, silica and volatile diluent leaving a flexible, protective film or coating over the injured area, the film or coating comprising a blend of non-volatile silicone oil and silica having the consistency of a stiff cream or a grease.

The non-volatile silicone oil component forms the base for the wound dressing and provides the chemical properties of the barrier between the injured tissue and the environment. Any silicone oil having a viscosity of at least about 5000 centistokes to about 200.000 centistokes or higher can be used for the wound dressings of the present invention, depending on the properties desired. The higher the viscosity of the silicone oil component, the more durable and removal resistant is the ultimate residual film covering the injured area. The lower the viscosity of the silicone oil component, the more easily can the wound dressing be applied to the injured area and the more easily can it be removed when required. By using the full range of silicone oil viscosities, the wound dressing can be tailored to the unique needs of each case. Silicone fluids having viscosities of about 30.000 centistokes are preferred as they provide a balance of residual film durability and ease of applicability. Most preferred is silicone fluid SF 200 having a viscosity of about 30,000 centistokes produced by Dow-Corning Inc. (Midland. Mich.) or any other generally equivalent silicone fluid produced by other silicone oil manufacturers.

The amorphous fumed silica provides a micro-skeletal structure when dispersed in the silicone oil that interacts with the silicone oil component and forms a gel. The viscosity of the original silicone oil is dramatically increased when blended with suitable quantities of fumed silica to that of a non-fluid grease-like gel. Any amorphous fumed silica that suitably thickens the silicone oil component may be used. Such fumed silicas include both untreated types and types that have been chemically treated to alter the fumed silica surface. Examples of suitable fumed silicas include but are not limited to Aerosil® 90, 130, 150, 200, 300, 380, R202, R805, R812, R972, R974 (Degussa Corporation, Ridgefield Park, N.J.) and CAB-O-SIL® TS-720 and M-5 (Cabot Corporation, Tuscola, Ill.). Generally, Aerosil® 200, Aerosil® R974, CAB-O-SIL® TS-720 and any other generally equivalent products from other manufacturers of fumed silicas are preferred as they suitably thicken silicone oils. The larger the quantity of fumed silica in the blend, the firmer is the resultant gel.

Compositions containing from about 0.5% to about 12% fumed silica based on the weight of the silicone oil component are preferred as they provide consistencies that make useful wound dressings. More preferred are compositions containing from about 1% to about 4% fumed silica based on the weight of the silicone oil component as they provide a balance of thickness and workability.

The volatile component provides a vehicle for loosening or reducing the viscosity of a silicone oil blend that is too thick to spread on an injured area, without causing further pain or injury, to a level which makes it readily spreadable or applicable by other means such as spraying. Within minutes of application, the volatile component evaporates from the loosened reduced viscosity blend leaving a protective wound dressing film residue having the consistency of a stiff cream in place on the wounded area. The properties of the residual silicone oil-silica blend are unaltered after evaporation of the volatile component. In some cases, such as extremely viscous silicone oil-silica blends, traces of volatile component may remain in the composition after application, but they are eventually driven off by body heat. The volatile component may be any suitable fluid that can dissolve or disperse a silicone oil-fumed silica mixture and that is also volatile at or around room temperature. Volatile silicone fluids are preferred as they are generally most compatible with silicone oils. Examples of suitable volatile silicone fluids are Dow-Corning 244 which comprises the cyclomethicone octamethylcyclotetrasiloxane and Dow-Corning 245 +1which comprises the cyclomethicone decamethylcyclopentasiloxane and other similar silicone fluids produced by other manufacturers. Mixtures of volatile silicone fluids may also be used to alter the rate of volatilization if desired. The volatile component can be added to the silicone oil-fumed silica blend in any proportion required to reduce the viscosity to an easy to apply oil or light grease. At very high dilution, for example 1 part of silicone oil-fumed silica blend to 1000 parts of volatile component, the product can be applied as a mobile fluid with a suitable applicator or even as a spray from a spray bottle. At the other extreme, as little as 1% of the volatile fluid can be added to the more fluid silicone oil-silica blends to assist in their application. The useful range of the volatile component therefore is from about 1% to about 99.9% by weight of the final mixture of silicone oil, fumed silica and volatile component.

The wound dressings of the present invention may be prepared by stirrers, blenders, mills and the like, and any other means known in the art for blending silicone oils and fumed silica. In addition pressure vessels, condensing systems and other means known in the art and commonly used to retain a volatile component in a mixture may be employed in the preparation of the wound dressings of the present invention. Generally, the silicone oil-fumed silica blend is first prepared and then admixed with the volatile diluent. However, in some cases the components comprising, silicone oil, fumed silica and volatile diluent may be combined in one stage to form the wound dressings of the present invention. For wound dressings tailored to specific needs, the method of blending previously prepared silicone oil-fumed silica blends to a desired consistency with the volatile diluent is most convenient.

Use of a volatile diluent provides enormous flexibility in the preparation of silicone based wound dressings since the non-volatile residue can be made to any desired viscosity and protective resistance to smearing or inadvertent removal by simply increasing or decreasing the proportion of silica, and yet still be applied without causing further injury or undue pain.

The flexibility offered by the practice of the present invention permits a complete range of physical properties to be obtained that are appropriate to the stage at which the wound dressing is used. A very fluid consistency may be obtained for the purpose of easy application to an injured skin area without pain, while the residual film left after evaporation can have the physical properties ideally suited for good adhesion to and protection of the wound or scar area. As the residual film may have a high viscosity, a sufficient thickness of wound dressing may be built up over the wound or scar area, which will generally remain in place over the wounded area, to control water vapor loss from the injured area. Without the addition of volatile oil, the viscosity of the residual evaporated film and consequently, the properties useful in a wound dressing that are associated with it, could not be adjusted through a broad range suitable for treatment of a wide variety of skin wounds and scars.

Although the present invention has been described in considerable detail with reference to certain preferred versions thereof, other versions are possible. Therefore, the spirit and scope of the appended claims should not be limited to the description of the preferred versions contained herein.

What is claimed is:

1. A wound dressing comprising a mixture of:
   a blend of silicone fluid and about 0.5% to about 12% fumed silica based on the weight of the silicone fluid, with the blend having a first consistency, with the first consistency being the consistency of a stiff cream, and
   about 1% to about 99.9% of a volatile diluent based on the weight of the final mixture, with the mixture having a second consistency, and with the second consistency being the consistency of a spreadable cream,
   so that the mixture can be easily applied to a wound, and a protective covering comprising the blend of silicone fluid and fumed silica having the first consistency, will remain on the wound upon evaporation of the volatile diluent.

2. The wound dressing of claim 1 in which the blend of silicone fluid and fumed silica contains about 1% to about 4% turned silica.

3. The wound dressing of claim 1 in which the volatile diluent comprises a volatile silicone fluid.

4. A wound dressing for the treatment of scars and wounds to the skin prepared in steps comprising:
   a) forming a blend comprising silicone fluid and about 0.5% to about 12% fumed silica based on the weight of the silicone fluid, the blend having a first consistency, with the first consistency being the consistency of a stiff cream;
   b) mixing the blend of step a) with about 1% to about 99.9% of a volatile diluent based on the weight of the final mixture, to form a mixture of silicone fluid, fumed silica and volatile diluent, with the mixture having a second consistency, and with the second consistency being the consistency of a spreadable cream.

5. The wound dressing of claim 4 in which the first consistency is the consistency of a grease, and the second consistency is the consistency of an oil.

6. The wound dressing of claim 4 in which the volatile diluent comprises a volatile silicone fluid.

7. A process for forming a protective coating of viscous silicone grease on a wound comprising the steps of:
   a) forming a viscous grease from a silicone fluid and about 0.5% to about 12% fumed silica based on the weight of the silicone fluid;
   b) mixing the viscous grease formed in to about 99.9% of a volatile diluent based on the weight of the final mixture, to form a mobile fluid;
   c) applying the mobile fluid formed in step b) to the wound so that the mobile fluid coats the wound;
   d) allowing the volatile diluent to volatilize from the mobile fluid applied to the wound in step c) thereby forming a residual coating comprising the viscous grease formed in step a) that protects the wound.

8. The process of claim 7 in which the viscous grease formed in step a) is a gel.

9. The process of claim 7 in which the volatile diluent of step b) comprises a volatile silicone fluid.

10. The process of claim 7 in which step c) comprises spraying the mobile fluid formed in step b) on the wound so that the mobile fluid coats the wound.

11. The wound dressing of claim 3 in which the volatile diluent comprises a volatile silicone fluid selected from the group consisting of octamethylcyclotetrasiloxane, decamethylcyclotetrasiloxane and mixtures thereof.

12. The wound dressing of claim 6 in which the volatile diluent comprises a volatile silicone fluid selected from the group consisting of octamethylcyclotetrasiloxane, decamethylcyclotetrasiloxane and mixtures thereof.

13. The process of claim 9 in which the volatile diluent comprises a volatile silicone fluid selected from the group consisting of octamethylcyclotetrasiloxane, decamethylcyclotetrasiloxane and mixtures thereof.

14. The wound dressing of claim 2 in which the blend of silicone fluid and fumed silica comprises a silicone fluid having a viscosity of about 30,000 centistokes.

* * * * *